(12) United States Patent
Diaz Carmena et al.

(10) Patent No.: US 10,474,839 B2
(45) Date of Patent: Nov. 12, 2019

(54) SYSTEM AND METHOD FOR CONTROLLING ACCESS TO A MEDICAL DEVICE

(71) Applicant: SOCIEDAD ESPANOLA DE ELECTROMEDICINA Y CALIDAD, SA, Algete (Madrid) (ES)

(72) Inventors: Angel Diaz Carmena, Alcorcon (ES); David Garcia Godoy, Leganes (ES); Carlos Rodriguez Gonzalez, Torrejon de Ardoz (ES); Jose Antonio Gonzalez Romera, Madrid (ES)

(73) Assignee: SOCIEDAD ESPANOLA DE ELECTROMEDICINA Y CALIDAD, S.A., Algete (Madrid) (ES)

( * ) Notice: Subject to any disclaimer, the term of this patent is extended or adjusted under 35 U.S.C. 154(b) by 0 days.

(21) Appl. No.: 16/284,872

(22) Filed: Feb. 25, 2019

(65) Prior Publication Data

US 2019/0188413 A1 Jun. 20, 2019

Related U.S. Application Data

(63) Continuation of application No. 15/644,370, filed on Jul. 7, 2017, now Pat. No. 10,216,955.

(51) Int. Cl.
G06F 21/62 (2013.01)
G07C 9/00 (2006.01)
(Continued)

(52) U.S. Cl.
CPC .......... G06F 21/6245 (2013.01); G06F 21/31 (2013.01); G06F 21/35 (2013.01);
(Continued)

(58) Field of Classification Search
CPC .............................. G06F 21/6245; G06F 21/31
(Continued)

(56) References Cited

U.S. PATENT DOCUMENTS 6,664,893 B1 12/2003 Eveland et al.
2008/0222734 A1* 9/2008 Redlich .................. G06F 21/577
726/26

(Continued)

Primary Examiner — Allen T Cao
(74) Attorney, Agent, or Firm — Neal, Gerber & Eisenberg LLP

(57) ABSTRACT

Systems, devices, and methods for controlling access to a medical device are provided. One example system includes an access card configured to wirelessly transmit user identification information and a medical device configured to receive the user identification information from the access card, and enable access to one or more components of the medical device based on permission information associated with the received user identification information. One example medical device includes a plurality of device components; a data receiver configured to wirelessly receive user identification information; a memory configured to store permission information in association with the user identification information; and a processor configured to retrieve the permission information from the memory in response to receiving the user identification information from the data receiver, and enable access to the one or more device components based on the retrieved permission information.

19 Claims, 7 Drawing Sheets

(51) Int. Cl.
*G06F 21/31* (2013.01)
*G16H 40/63* (2018.01)
*G06F 21/35* (2013.01)
G06F 19/00 (2018.01)
G16H 30/20 (2018.01)

(52) U.S. Cl.
CPC ...... *G07C 9/00007* (2013.01); *G07C 9/00111* (2013.01); *G16H 40/63* (2018.01); *G06F 19/321* (2013.01); *G16H 30/20* (2018.01)

(58) Field of Classification Search
USPC .................................. 340/5.6–5.65
See application file for complete search history.

(56) References Cited

U.S. PATENT DOCUMENTS

| | | | |
|---|---|---|---|
| 2009/0258335 A1* | 10/2009 | Marmaropoulos | G09B 23/286 434/262 |
| 2010/0295686 A1 | 11/2010 | Sloan et al. | |
| 2011/0004076 A1* | 1/2011 | Janna | A61B 5/0031 600/302 |
| 2012/0185268 A1* | 7/2012 | Wiesner | G06F 19/3418 705/2 |
| 2013/0200999 A1 | 8/2013 | Spodak et al. | |
| 2014/0007154 A1* | 1/2014 | Seibold | H04N 21/4122 725/25 |
| 2014/0098943 A1 | 4/2014 | Omura et al. | |
| 2015/0035643 A1 | 2/2015 | Kursun | |
| 2015/0070187 A1* | 3/2015 | Wiesner | A61B 5/0022 340/870.02 |
| 2015/0186834 A1 | 7/2015 | Mickles et al. | |

* cited by examiner

SYSTEM AND METHOD FOR CONTROLLING ACCESS TO A MEDICAL DEVICE

CROSS-REFERENCE TO RELATED APPLICATIONS

This application is a continuation of U.S. patent application Ser. No. 15/644,370, filed on Jul. 7, 2017 and entitled "System and Method for Controlling Access to a Medical Device," the contents of which are incorporated herein in their entirety.

TECHNICAL FIELD

This application generally relates to medical devices and more specifically, to controlling access to or usage of such devices.

BACKGROUND

Hospitals, clinics, and other healthcare facilities typically house numerous medical devices or machines for performing medical procedures, scans, or tests on patients, entering information about patients, or otherwise treating patients. The medical devices can include, for example, x-ray machines, ultrasound machines, and other medical imaging devices, electrocardiogram (EKG) machines, blood-draw carts, computer work stations, etc. Some of these machines are portable units, or movable from one location to another using castors or wheels included on the unit. Other machines are stationary units, or fixed to a single location, for example, due to the size, weight, and/or complexity of the machine.

Typically, only authorized healthcare personnel are allowed to operate the medical devices located in a healthcare facility. In some cases, a user may be asked to present valid credentials (such as, e.g., a login and password or an identification card) before operating or otherwise gaining access to a medical device. Security measures may also be taken to protect patient information stored on the medical devices, or medical information obtained using the machines, in accordance with healthcare regulations, such as HIPAA in the United States. However, existing security measures do not adequately control the different types of use that may need access to certain persons for a given medical device, the tasks specifically associated with each type of user, or verification of the training and other qualifications that may be required to perform each task. As a result, some users may be given more access than necessary or appropriate.

For example, service persons may be given full access to a medical device when performing repairs or maintenance. However, such users may only require access to the physical components of the medical device and/or any error logs stored on the device, and should not be given access to any private patient information stored on the device. Similarly, clinical healthcare workers, including doctors, nurses, and patient care technicians, may be given full access to a medical device when performing procedures or providing patient care, but limited or prohibited access to functions reserved for service persons. Further, clinical users do not need access to certain administrative or maintenance features of the device, such as, e.g., event logs and error logs, and not all of the clinical workers of a particular facility may have the training or authorization to operate a particular use of the medical device. As yet another example, portable medical devices may be equipped with security measures, such as lockable wheels or padlocks for securing the device to one location when not in use, to prevent removal by unauthorized users, as an anti-theft measure and to assure the location of the equipment is as intended, ready for use when needed. In some cases, unlocking the anti-theft security measures also unlocks the operational features of the medical device. However, some non-clinical workers, such as equipment transport personnel and janitorial staff, only need the ability to move the medical device from one location to another, and should not have access to the operational or other functions of the medical device.

Accordingly, there is a need in the art for techniques that can tailor the access privileges for each authorized user of a medical device to match the user's qualifications, job description, and/or other marker for selecting an appropriate level of access to the device.

SUMMARY

The invention is intended to solve the above-noted and other problems by providing systems and methods configured to control access to medical devices by, among other things, (1) providing each user of a medical device an access card that is linked to the user's access privileges, (2) requiring all users to present the access card to the medical device in order to use the device, and (3) enabling access to select components of the medical device based on the access privileges associated with the access card presented to the device.

For example, one embodiment provides a medical device, comprising: a plurality of device components; a data receiver configured to wirelessly receive user identification information; a memory configured to store permission information in association with the user identification information, the permission information identifying one or more of the device components as being permissible for access by the user; and a processor in communication with the memory, the data receiver, and the plurality of device components. The processor is configured to retrieve the permission information from the memory in response to receiving the user identification information from the data receiver, and enable access to the one or more device components based on the retrieved permission information.

Another example embodiment provides a method of controlling access to a medical device. The method comprises wirelessly receiving identification information for a user via a data receiver; retrieving permission information associated with the received identification information from a memory, the permission information identifying one or more components of the medical device as being permissible for access by the corresponding user; and enabling, using a processor, access to each component identified by the retrieved permission information.

Yet another example embodiment provides an electronic device communicatively coupled to a medical device. The electronic device comprises a memory for storing identification information and associated permission information for a plurality of users. The permission information identifies one or more components of the medical device as being permissible for access by the corresponding user. The electronic device also includes a data receiver for wirelessly receiving user identification information and a processor in communication with the memory and the data receiver. The processor is configured to: receive the user identification information from the data receiver; retrieve, from the memory, the permission information associated with the received user identification information; and transmit instructions to the medical device for enabling access to the one or more device components identified by the retrieved permission information.

Still another example embodiment includes a system comprising an access card configured to wirelessly transmit user identification information and a medical device configured to: receive the user identification information from the access card, and enable access to one or more components of the medical device based on permission information associated with the received user identification information, the permission information identifying the one or more of the components as being permissible for access by the user.

As will be appreciated, this disclosure is defined by the appended claims. The description summarizes aspects of the embodiments and should not be used to limit the claims. Other implementations are contemplated in accordance with the techniques described herein, as will be apparent to one having ordinary skill in the art upon examination of the following drawings and detail description, and such implementations are intended to within the scope of this application.

BRIEF DESCRIPTION OF THE DRAWINGS

For a better understanding of the invention, reference may be made to embodiments shown in the following drawings. The components in the drawings are not necessarily to scale and related elements may be omitted, or in some instances proportions may have been exaggerated, so as to emphasize and clearly illustrate the novel features described herein. In addition, system components can be variously arranged, as known in the art. Further, in the drawings, like reference numerals designate corresponding parts throughout the several views.

DETAILED DESCRIPTION OF EXAMPLE EMBODIMENTS

Figure 1:
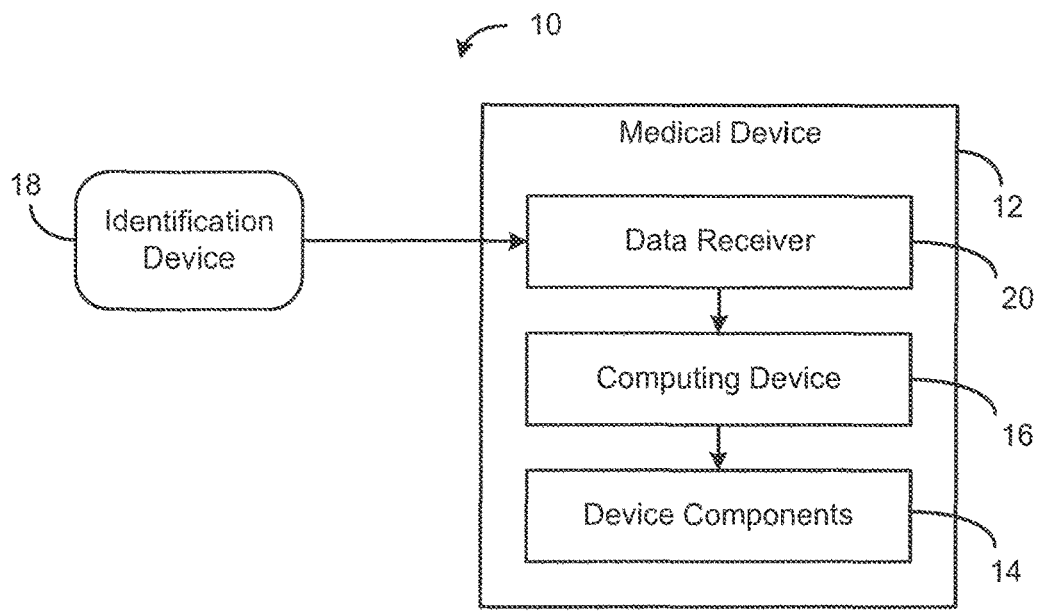
FIG. 1 is a block diagram of an example system for controlling access to a medical device in accordance with certain embodiments.

While the invention may be embodied in various forms, there are shown in the drawings, and will hereinafter be described, some exemplary and non-limiting embodiments, with the understanding that the present disclosure is to be considered an exemplification of the invention and is not intended to limit the invention to the specific embodiments illustrated.

In this application, the use of the disjunctive is intended to include the conjunctive. The use of definite or indefinite articles is not intended to indicate cardinality. In particular, a reference to "the" object or "a" and "an" object is intended to denote also one of a possible plurality of such objects.

FIG. 1 illustrates an exemplary system 10 for controlling user access to a medical device 12 (such as, e.g., portable x-ray machine 100 shown in FIGS. 2A-5) in accordance with embodiments. The medical device 12 includes a plurality of components 14 (also referred to herein as "device components") that may be used or accessed during operation, transportation, maintenance, or configuration of the medical device 12 and/or other actions involving the device 12. Each of the device components 14 can be individually or independently controlled (e.g., turned on or off, made available or not available, etc.) using a computing device 16 included in the system 10, and can comprise hardware, software, or a combination of both.

Figure 5:
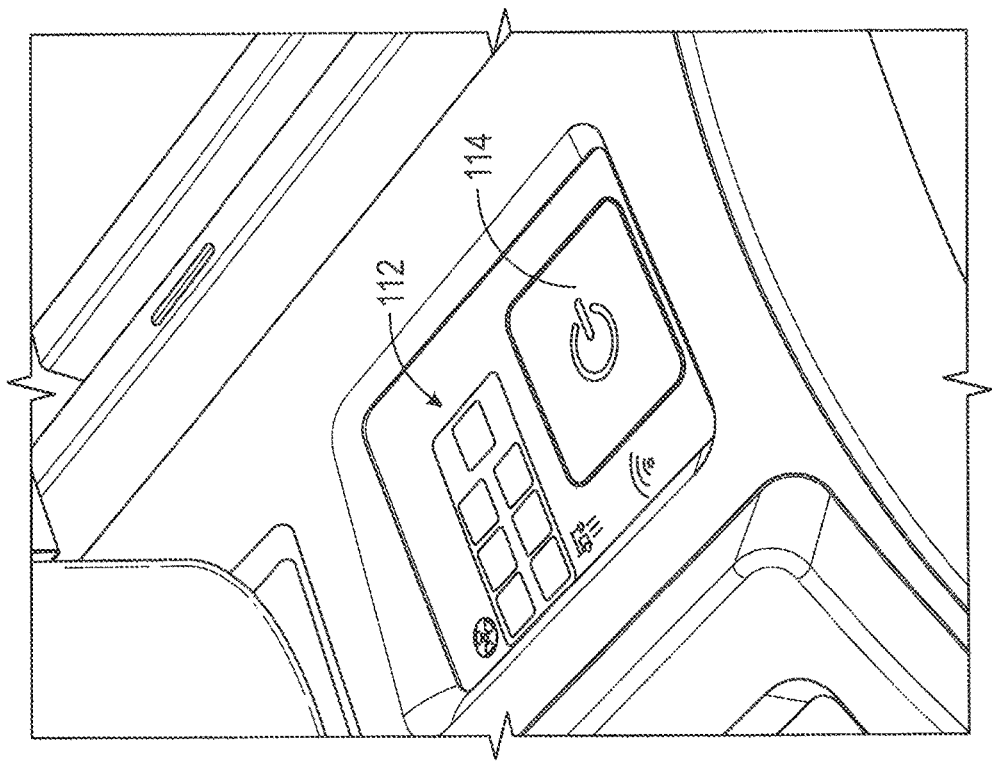
FIG. 5 is a close-up view of an exemplary access card placed on the control panel shown in FIG. 4, in accordance with certain embodiments.
Figure 6:
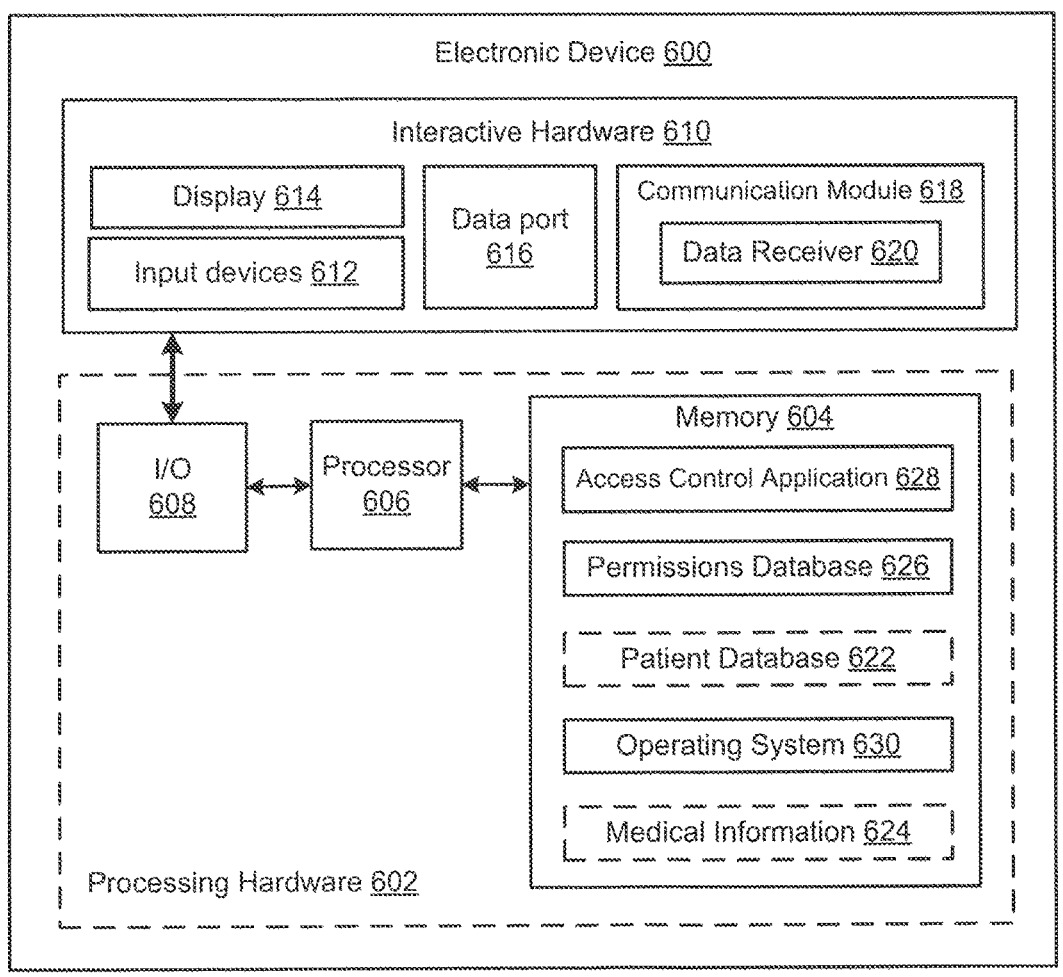
FIG. 6 is a block diagram of an example electronic device communicatively coupled to a medical device in accordance with certain embodiments.

As an example, the device components 14 may include one or more of the following: an on/off button, a log-on/log-off option, a service mode, an administrator mode, a calibration or configuration mode, a locking mechanism or other security device for preventing access to the medical device 12 (such as, e.g., locking mechanism 106 shown in FIG. 2A), a user interface for allowing a user to operate the medical device 12 (such as, e.g., user interface 110 shown in FIG. 3B), equipment for providing patient care (such as, e.g., x-ray generator 108 shown in FIG. 2A, other medical imaging device), one or more databases stored in a memory of the medical device 12 (such as, e.g., patient database 622 shown in FIG. 6, error logs database, event logs database, etc.), one or more data ports for retrieving medical data from the medical device 12 (such as, e.g., data port 616 shown in FIG. 6), and a wireless communication module for receiving data from, or transmitting data to, a remote server via a wireless communication network (such as, e.g., communication module 618 shown in FIG. 6). For portable or mobile medical devices 12, such as, e.g., portable x-ray machine 100 shown in FIGS. 2A-5, the device components 14 may also include a transportation system (e.g., wheels), and possible motor-driven controllable movement, for moving the medical device 12 from one location to another (such as, e.g., transportation system 104 shown in FIG. 2A) and/or a security device for securing or fixing the medical device 12 to one place. It should be appreciated that the exact number and type of components included in the medical device 12 will vary depending on the purpose and operational capabilities of the device 12.

In embodiments, each authorized user of the medical device 12 can be associated with a set of personalized access privileges, or permission information, that determines which of the device components 14 are permissible for access by the user and which components 14 are not permissible for access. The permission information may be tailored to specific characteristics of the user, including, for example, occupation, responsibilities associated with the occupation, and training or other qualifications pertinent to operation of the medical device 12. In some embodiments, each user may be given only the minimum level of access required to complete the tasks assigned to the user or to the user's position at the healthcare facility. For example, access privileges for a service worker may be restricted to the device components 14 that are needed to service, repair, or otherwise perform maintenance of the medical device 12 and may not include access to a patient database, including, for example, a patient list or patient history. As another example, access privileges of janitors may include access to only the transportation system of the medical device 12, so that the device 12 can be moved as needed while cleaning an area including the device 12, and may not include any other device components 14. In some cases, the access privileges may be configured so that the user can turn on the device 12, unlock one or more components 14 of the device 12 in order to activate the transportation system, and steer the device 12 to a desired location, but cannot operate the device 12.

As yet another example, all clinical healthcare workers (e.g., nurses, lab technicians, physicians, and physician's assistants) may be given access to the patient list and to the device components 14 related to operating the medical device 12 and providing patient care (e.g., user interface, medical equipment, on/off button, locking mechanism, transportation system, etc.), as well as access to the data port for downloading medical data from the medical device 12 and/or the wireless communication module for uploading medical data to a remote server. However, only lab technicians may be given access to the configuration or calibration mode of the medical device 12, while only nurses, physicians, and physician's assistants may be given access to patient history information in order to protect the confidentiality of the patients. Further, clinical healthcare workers, as a whole, may not be given access to operation in the service mode or the administrator mode like server works or administrators, respectively. In some cases, the access privileges for clinical healthcare workers may be restricted based on whether they have completed certain prerequisites for using the medical device 12, such as, for example, training seminars or other certifications.

In other embodiments, the permission information includes a permission level chosen from a hierarchy of permission levels that relate to the user's occupation and/or level of experience. For example, certain clinical healthcare workers (e.g., nurses, physicians, and physician's assistants) may be given a first permission level that is considered higher (e.g., provides more access) than a second permission level granted to other types of clinical healthcare workers (e.g., lab technicians). In such cases, both permission levels may enable operation of the medical device 12 and provide user access to a patient list for the medical device 12. However, only the first permission level may provide user access to a patient database comprising patient history information, in order to protect the confidentiality of the patients.

The computing device 16 can be configured or adapted to determine the personalized access privileges associated with a given user of the medical device 12 and enable user access to the medical device 12 based on the identified privileges. The computing device may include a memory or data storage device and a data processor to carry out the techniques described herein. An example of the computing device 16 may be electronic device 600 shown in FIG. 6. In embodiments, the computing device 16 utilizes identification information received from an identification device 18 of the user to determine which access privileges are associated with the user. For example, each authorized user of the medical device 12 may be assigned a unique identification device 18 that must be presented to the computing device 16 to obtain access to the medical device 12. Each identification device 18 stores identification information (also referred to herein as "user identification information") that is associated with the corresponding user and/or the access privileges that are assigned to that user. As shown in FIG. 1, the system 10 further includes a data receiver 20 communicatively coupled to the identification device 18 and the computing device 16. In embodiments, the data receiver 20 receives the identification information from the identification device 18 and provides the received information to the computing device 16.

The identification device 18 may be any type of device capable of storing identification information thereon and of wirelessly communicating the stored information to the data receiver 20. In one example embodiment, the identification device 18 is embedded in an access card (such as, e.g., access card 102 shown in FIG. 5) or other ID card or key card that is assigned to a particular user and can be used to access the medical device 12 and other medical devices within a healthcare facility. In other embodiments, the identification device 18 may be included in a key fob, a wearable article (e.g., bracelet, lanyard, etc.), or other item that can be easily carried by the user and presented to, or detected by, the medical device 12 when access is required.

In some embodiments, the identification information received from the identification device 18 includes user information (e.g., name, a user ID number, etc.) for uniquely identifying the user. In other embodiments, the identification information includes a device identifier (ID) or other information for uniquely identifying the identification device 18.

Upon receiving the identification information, the computing device 16 retrieves permission information associated with the received information from a memory (such as, e.g., memory 604 shown in FIG. 6) of the computing device 16. In embodiments, the memory of the computing device 16 includes one or more databases (e.g., permissions database 626 shown in FIG. 6) for storing the unique identification information for each user in association with the permission information, or access privileges, assigned to that user. For example, the permissions database may be a look-up table comprising a plurality of identification information entries and the permission information associated with each entry. The permission information, itself, may include a list of device components 14 that are accessible to the user and/or a list of components 14 that are not accessible to the user. The permissions database may store the permission information for each user in association with the device ID and/or the user information associated with that user, depending on the content of the identification information. In some cases, the computing device 16 uses the device ID to identify user information for the user associated with the identification device 18, before locating the access privileges assigned to that user.

In some embodiments, the data receiver 20 may be included in, or part of, an active transceiver (not shown) configured to transmit a signal requesting identification information (e.g., an interrogator signal) to the identification device 18. In such cases, the identification device 18 receives the signal once the device 18 is located within a predetermined range of the data receiver 20 and in response, sends a signal comprising identification information to the data receiver 20. In other embodiments, the data receiver 20 may be a passive receiver configured to wait for a signal from the identification device 18. In such cases, the identification device 18 periodically transmits a signal comprising identification information, and the data receiver 20 may detect and receive the signal once the identification device 18 is located within the predetermined range of the data receiver 20. In some cases, the predetermined range may be configured so that data communication occurs once the identification device 18 is adjacent to (or within close proximity of) the data receiver 20. In other cases, the predetermined range may be configured so that data communication occurs only after the identification device 18 is in contact with the data receiver 20 and/or the medical device 12, to make sure that only the intended medical device 12 is made accessible to the user.

In embodiments, the identification device 18 can be configured to communicate the user identification information to the data receiver 20 using a wireless personal area network (WPAN), such as, e.g., radio frequency identification (RFID), near field communication (NFC), Bluetooth, Zigbee, infrared, or other short-range communication network. Likewise, the data receiver 20 can be a short-range wireless receiver or transceiver configured to facilitate WPAN communications. In a preferred embodiment, the identification device 18 is an RFID tag configured to transmit a radio signal containing the identification information, and the data receiver 20 is an RFID reader configured to receive the radio signals transmitted by the RFID tag.

As shown in FIG. 1, the computing device 16 can be communicatively coupled to the device components 14, via wired or wireless connections, to control user access thereto based on the retrieved permission information. In embodiments, the computing device 16 can enable access to the permissible component(s) 14 of the device 12 and/or prevent access to the non-permissible component(s) 14, as outlined by the personalized access privileges associated with the user. For example, if the access privileges allow operational access to the medical device 12, and one of the device components 14 is a security system, the computing device 16 may send an unlock command to the security system to unlock the medical device 12, once the identification device 18 is within the predetermined range of the data receiver 20.

In the illustrated embodiment, the computing device 16 is included in, or integrated with, the medical device 12. In other embodiments, the computing device 16 may be a separate unit from the medical device 12, but may still be communicatively coupled to the medical device 12, for example, via a wired or wireless connection. In still other embodiments, a portion of the computing device 16 may be included in the medical device 12 and a remainder of the computing device 16 (e.g., the permissions database) may be situated at a separate location (e.g., stored on a remote server). The illustrated embodiment also shows the data receiver 20 as being included in the medical device 12 separate from the computing device 16. In other embodiments, the data receiver 20 may be included in the computing device 16, for example, as shown by data receiver 620 in FIG. 6.

FIGS. 2A through 5 illustrate an example medical device 100 configured to control user access thereto based on access privileges associated with the user, in accordance with embodiments. While the illustrated embodiment shows a specific medical device, a portable x-ray machine, it should be appreciated that the techniques described herein can be used with any type of medical device, including small mobile units and large stationary machines.

In embodiments, the medical device 100 may be similar to the medical device 12 shown in FIG. 1. For example, the medical device 100 includes a data reader (not shown) configured to wirelessly receive user identification information from an access card 102 presented to or at the medical device 100, similar to the data receiver 20 and the identification device 18 shown in FIG. 1. The medical device 100 also includes a processor and/or computing device (not shown) configured to identify access privileges for the user associated with the access card 102 based in the received identification information, similar to the computing device 16 shown in FIG. 1 and/or the electronic device 600 shown in FIG. 6.

In addition, the medical device 100 includes a plurality of components that enable operation, transportation, or other use of the device 100 and are individually controllable by the computing device depending on the access privileges of the user, similar to the device components 14 shown in FIG. 1. In the illustrated example, the medical device 100 is a medical imaging machine, such as, for example, a portable x-ray machine, that includes a transportation system 104 configured to allow movement of the machine from one location to the next (e.g., from one patient room to another). This movement capacity is provided by wheels at the base of the x-ray machine, and may include alternate structure for facilitating transport and may have motor-driven wheels which are capable of being controlled by a user having access for such control. The medical device 100 also includes a locking mechanism 106 for selectively preventing functional or operational access to the machine. In addition, the medical device 100 includes an imaging head 108 for performing medical imaging procedures (e.g., x-rays) and a user interface 110 for controlling operation of the x-ray machine 100. The medical device 100 can also include a control panel 112 for controlling on/off and log-in/log-off functions of the medical device 100. According to embodiments, each of the transportation system 104, the locking mechanism 106 (and/or motor drive assembly), the imaging head 108, the user interface 110, and the control panel 112, each can constitute one of the individually controllable components of the medical device 100. As will be appreciated, the medical imaging device 100 may include other components that are not described herein for the sake of brevity.

In embodiments, the transportation system 104 includes a locking mechanism (not shown) capable of placing the system 104 in, or activating, a locked mode that prevents transportation of the machine 100 and an unlocked mode that permits transportation of the machine 100. The locking mechanism may be electronically controllable by the computing device depending on the access privileges of the user. For example, in the illustrated embodiment, the transportation system 104 further comprises a plurality of wheels 104a and 104b on one side of the machine 100 and a similar set of wheels (not shown) on the opposite side of the machine 100. In such cases, the locking mechanism may be a lock included on each of the wheels 104 and capable of being electronically moved between a locked position for activating the locked mode and an unlocked position for activating the unlocked mode, based on the access privileges of the user. Alternatively, the locking mechanism may comprise a controllable motor drive assembly (no shown) which permits movement only when access to the motor drive control is provided and otherwise, the lack of motor driven movement of the wheels effectively locks the device in position. In other embodiments, instead of wheels, the transportation system 104 may include tracks, gliders, or any other suitable type of base configured for ground transportation, and an appropriate locking mechanism for selectively preventing unauthorized movement of the x-ray machine 100.

Figure 2A:
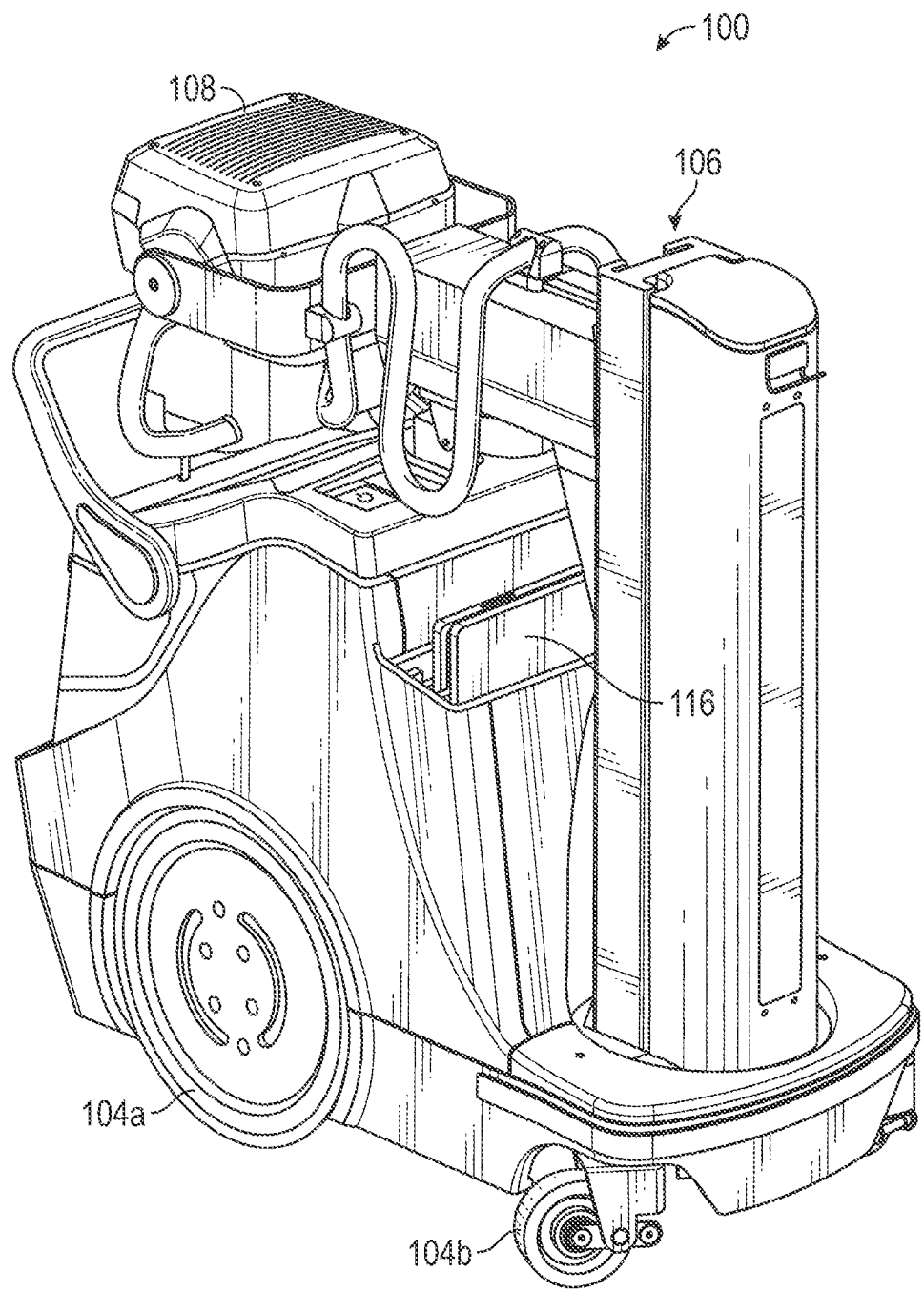
FIG. 2A is a rear perspective view of an example medical device, a mobile x-ray imaging device, which is in a closed position, in accordance with certain embodiments.
Figure 2B:
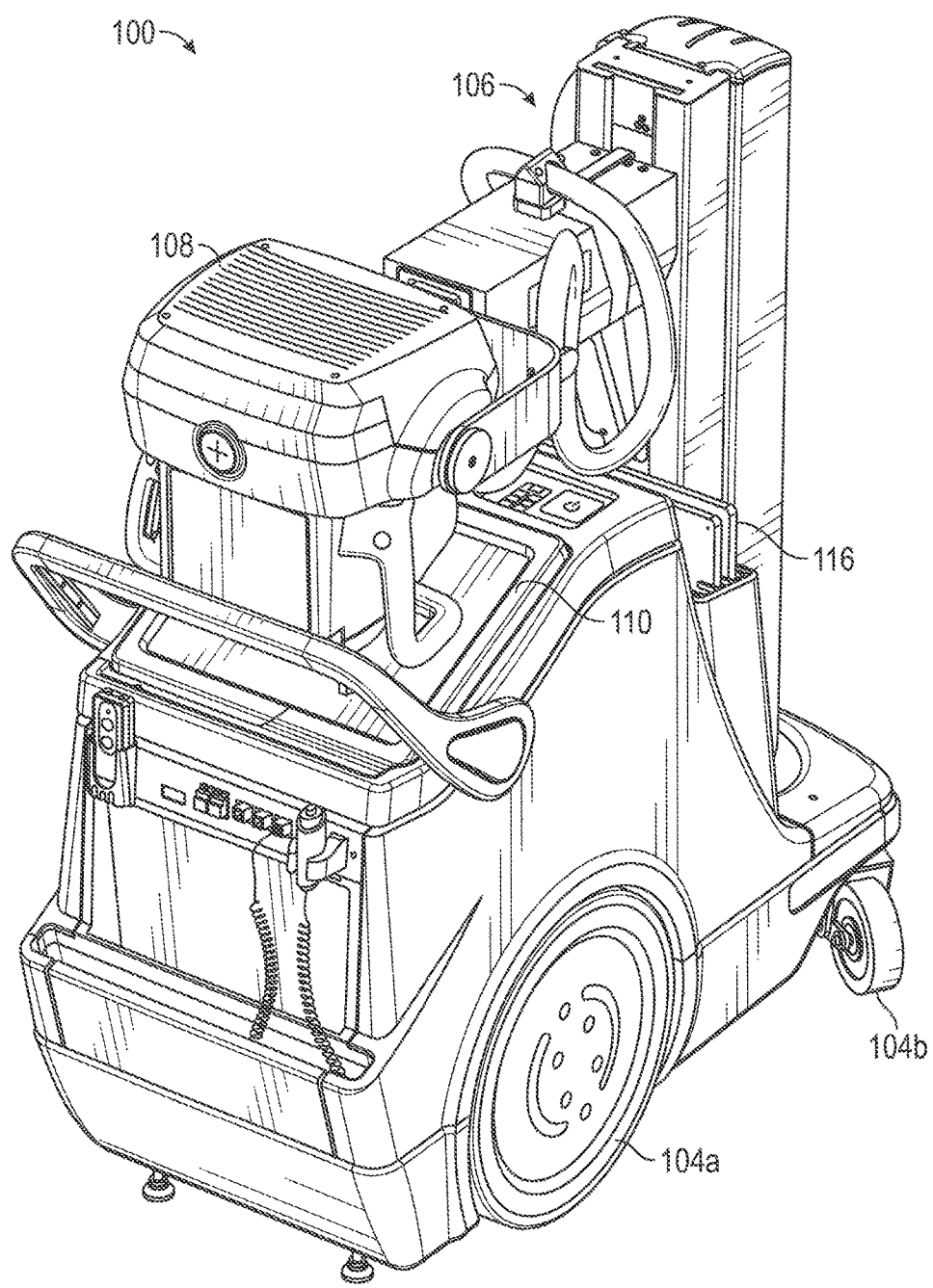
FIG. 2B is a front perspective view of the medical device shown in FIG. 2A, in accordance with certain embodiments.

To prevent unauthorized access to the medical imaging functions of the medical device 100, the functional locking mechanism 106 can be movable between a closed position for preventing operation of the device 100 (e.g., as shown in FIGS. 2A and 2B) and an open position for enabling medical imaging operation of the device 100 (e.g., as shown in FIG.

Figure 3A:
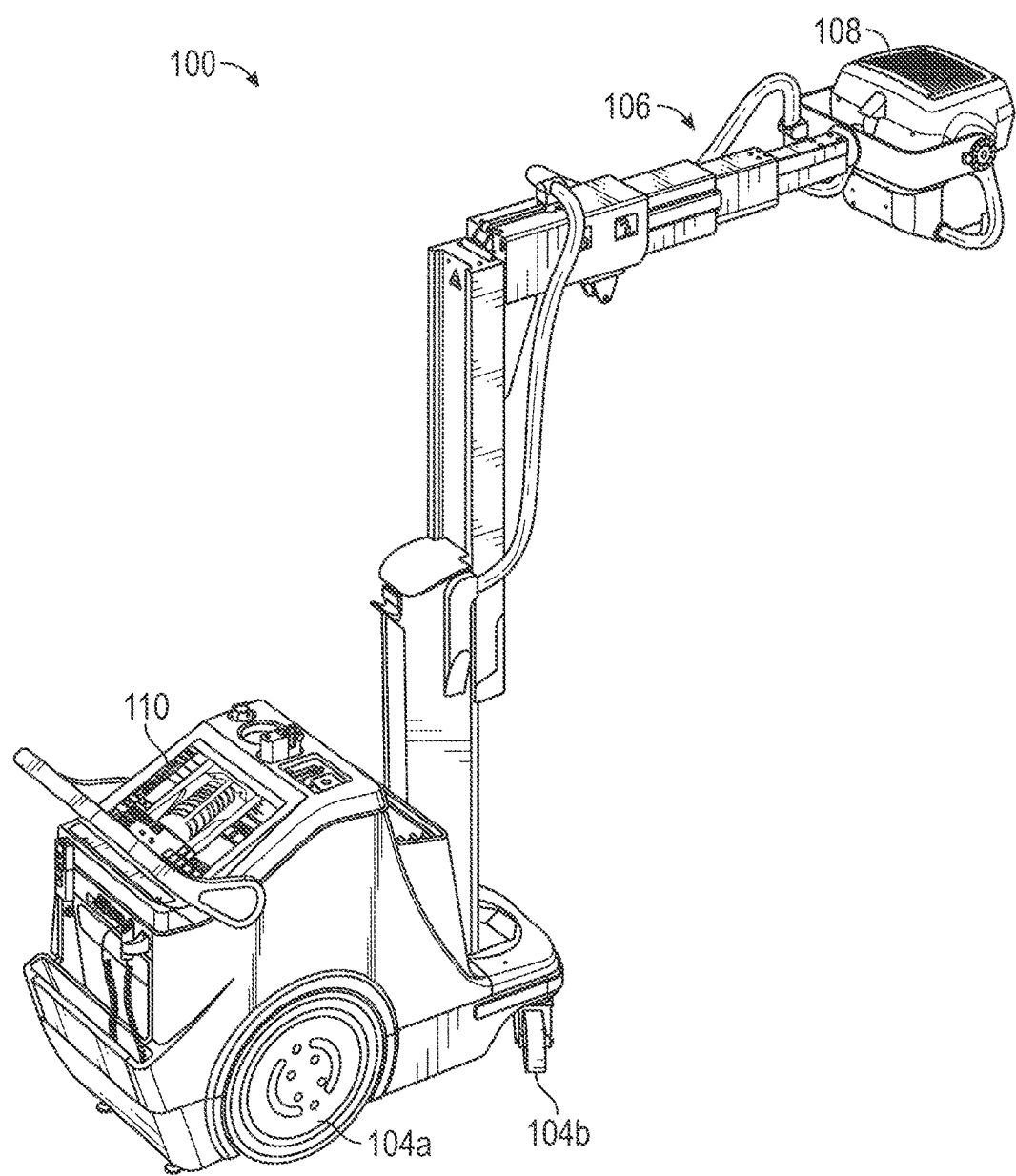
FIG. 3A is a front perspective view of the medical device of FIG. 2A in an open position, in accordance with certain embodiments.

3A). In embodiments, the computing device can be communicatively coupled to the locking mechanism 106 to electronically control the position of the locking mechanism 106. The medical device 100 may be placed in the closed position while the x-ray machine is not being used or is unavailable for operational use based on the user's access privileges, and may be placed in the open position while the x-ray machine is in use or is available for operational use based on the user's access privileges. In the illustrated embodiment, the closed position of the locking mechanism 106 is configured to physically block access to the user interface 110, the imaging head 108, and/or one or more other components of the portable x-ray machine 100, while the open position of the locking mechanism 106 is configured to provide full access to these and any other device components. More specifically, the locking mechanism 106 includes a support structure attached at one end to a body of the x-ray machine and at a far end to the imaging head 108. As shown in FIG. 3A, when the locking mechanism 106 is controlled to the open position, the support structure extends out from the body of the x-ray machine, making the imaging head 108 and user interface 110 unobstructed and fully accessible. As shown in FIGS. 2A and 2B, when the locking mechanism 106 is controlled to the closed position, the support structure is retracted and folded over the body of the x-ray machine, such that the imaging head 108 covers the user interface 110, making both components unavailable for use.

The imaging head 108 may include an x-ray generator or other image generator. In embodiments, the computing device can be communicatively coupled to the imaging head 108 to prevent unauthorized use of the medical imaging functions of the medical device 100. For example, the computing device can be configured to control an on/off function of the imaging head 108 based on whether access privileges of the user provide permission to take x-rays. In some embodiments, the imaging head 108 includes a swivel function that allows the imaging head 108 to be moved to different positions and capture x-rays at each of those positions. In such cases, the computing device may also be configured to control the swivel function (e.g., turn the function on or off) of the imaging head 108.

Figure 3B:
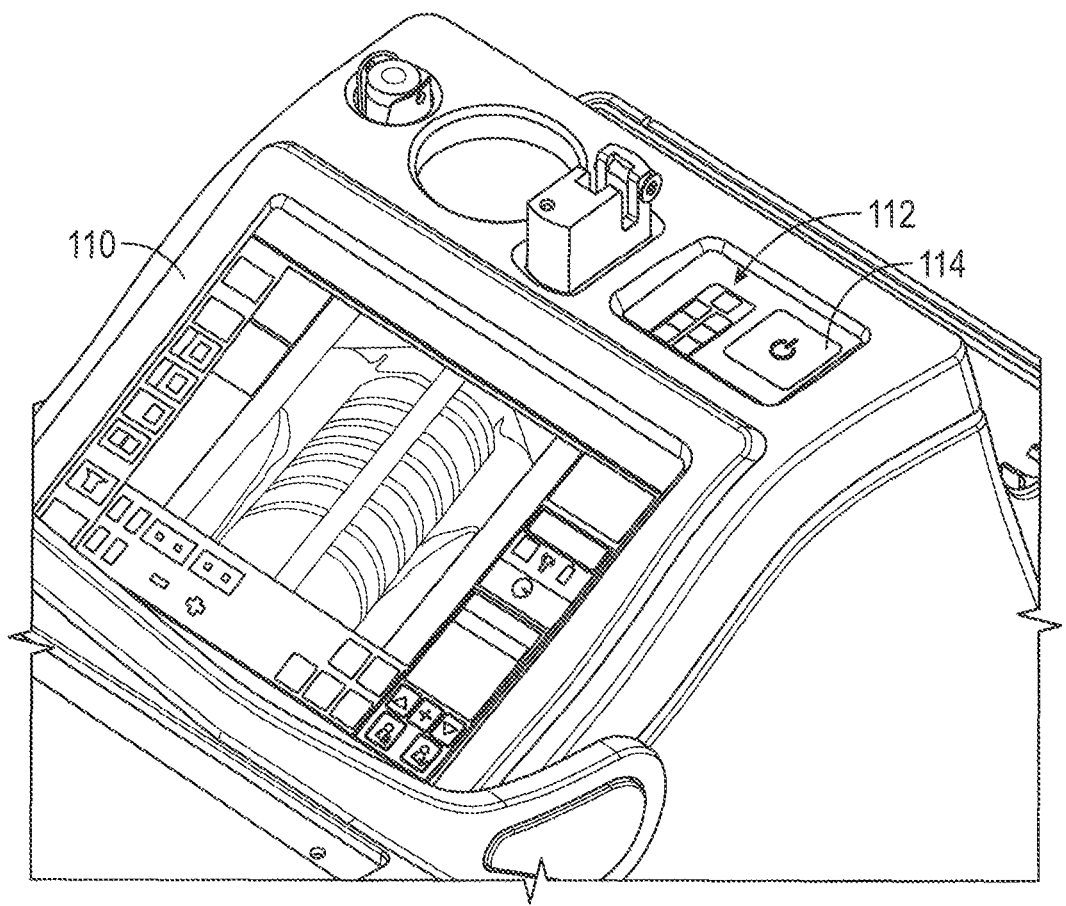
FIG. 3B is a close-up view of an exemplary user interface of the medical device shown in FIG. 3A, in accordance with certain embodiments.

As shown in FIG. 3B, the user interface 110 can include a plurality of input devices (e.g., buttons, soft keys, touch screen, etc.) for controlling various medical imaging functions of the machine 100 and a display screen for displaying x-rays or other medical images. In embodiments, the computing device can be communicatively coupled to the user interface 110 to prevent unauthorized operational access to the medical device 100 and/or limit the functions that can be controlled by the user. For example, the computing device can be configured to control an on/off function of the user interface 110 based on whether the access privileges of the user allow any operational access to the medical device 100. In the case of a janitor, for example, the user interface 110 may be turned off.

In some embodiments, the access privileges of the user may provide permission to access a select group of components included in the user interface 110, such as, for example, one or more of the input devices, the display screen, and/or one or more software components (e.g., menu options) accessible via the user interface 110. For example, if the user is only authorized to download medical imaging data from the x-ray machine 100, the user interface 110 may be turned on and generally accessible, but the input devices related to performing medical imaging procedures may be made unavailable or inaccessible to that user. As another example, menu options related to operating in an administration mode or otherwise performing administrative tasks, such as, e.g., writing, erasing, and/or modifying the permissions granted to each user of the machine, may be disabled for all users except administrative personnel. Similarly, menu options related to operating in a service mode or otherwise performing repair and maintenance activities may be disabled for all users expect service personnel.

As yet another example, the user interface 110 may be configured to prevent access to error logs (e.g., a list of the different errors that occurred during use of the machine) and/or event logs (e.g., descriptions of the types of activities performed and the date and time of performance) that are stored in a memory of the machine, if the user's access privileges do not specify such access. Also, the user interface 110 may be configured to prevent access to a configuration and calibration mode of the medical device 100 for users that are not allowed to modify these aspects of the equipment. As another example, the user interface 110 may be configured to prevent access to a patient list if the user does not have permissions related to performing medical procedures using the machine. Similarly, the user interface 110 may be configured to prevent access to patient history and pathology information stored in a patient database if the user does not have permissions related to treating and/or diagnosing patients.

As yet another example, the user interface 110 may be configured to prevent access to menu options that require Internet access to download or update software or firmware stored on the computing device or medical device 100, or otherwise perform remote servicing, if the access privileges of the user do not include servicing the x-ray machine or do not permit remote access while using the medical device 100. In some cases, the user permission information may also prevent usage of a wireless communication module included in the medical device 100, so that the user cannot access the Internet while using the machine.

Figure 4:
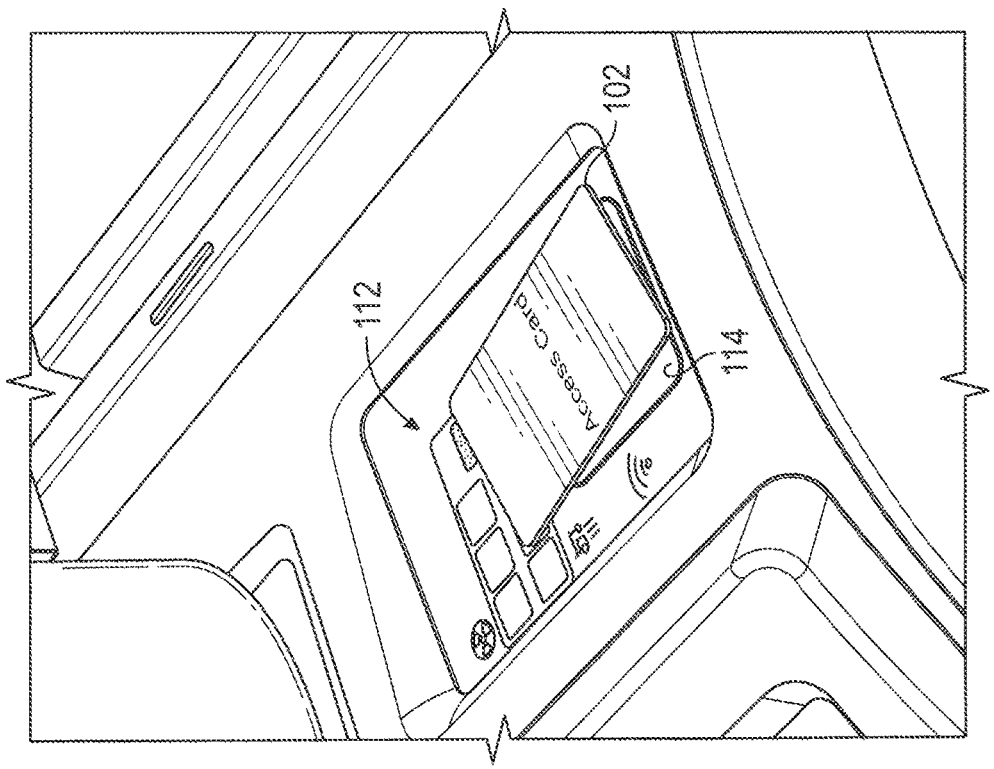
FIG. 4 is a close-up view of an exemplary control panel included in the user interface of FIG. 3B, in accordance with certain embodiments.

As shown in FIG. 4, the control panel 112 can include a number of input devices for controlling operation of the medical device 100, including a power button 114 for turning the medical device 100 on or off and a data receiver (not shown) for receiving identification information. In some cases, the control panel 112 may also include an input device (not shown) for logging users in and out of the machine. In embodiments, the computing device can be communicatively coupled to the control panel 112 to prevent unauthorized control of the medical device 100. For example, if the user does not have access privileges that permit operation of the medical device 100, the computing device may disable the power button 114 when that user is logged into the device 100. In some cases, the access privileges may indicate whether or not a user has shutdown privileges, and if they do not, the power button 114 may be disabled when the user logs into a machine that is already powered on.

In embodiments, a user may log into the medical device 100 by placing the access card 102 against, adjacent to, or above the power button 114 and/or the control panel 112. During the login process, the data receiver obtains identification information from the access card 102, for example, using RFID communication. Based on the received information, the computing device identifies the user associated with the access card 102 and determines which access privileges apply to that user. The login process may end once the computing device enables appropriate device components based on the access privileges associated with the access card 102. In some cases, the user may be required to press the access card 102 against the power button 114 in order to initiate the login process.

In some cases, the control panel 112 includes a user-selectable option to log off (not shown) from the medical device 100 without shutting down the machine. The log off option may be used, for example, once the user is done with a task and/or when the user needs to hand operation of the device 100 over to another authorized user. As an example, a lab technician may log off from the medical device 100 after performing a medical imaging procedure, so that the physician can log into the machine and view the results of the procedure, as well as patient history information.

As shown in FIGS. 2A and 2B, the medical imaging device 100 may further include x-ray detectors and grids 116 that can be securely stowed on the device 100 using a security mechanism (not shown). In embodiments, the computing device may control access to the detectors and grids 116 by locking or unlocking the security mechanism based on the permission information for a given user. For example, the x-ray detectors and grids 116 may be unlocked for users that are allowed to take x-rays or perform maintenance on the x-ray machine.

It should be appreciated that the examples provided herein are not an exclusive list of the types of permissions that may be provided and enforced using the techniques described herein. Each type of medical device and/or each hospital facility may lead to a unique set of permissions for each of its users.

Referring now to FIG. 6, shown is a block diagram of an example electronic device 600 for controlling access to a medical device, such as, for example, the medical device 12 shown in FIG. 1 or the portable x-ray machine 100 shown in FIGS. 2A-5, in accordance with embodiments. In some cases, the electronic device 600 may be included in the medical device, for example, like the computing device 16 of the medical device 12 shown in FIG. 1. In other cases, the electronic device 600 may be separate from the medical device but communicatively coupled thereto for carrying out the techniques described herein. In such cases, the electronic device 600 may transmit instructions to the medical device, for example, in order to control or enable access to one or more components of the medical device, in accordance with the techniques described herein. In some embodiments, the electronic device 600 may be representative of a computer utilized to implement method 700 shown in FIG. 7. The electronic device 600 can include any type of computing device, including one or more special or general purpose digital computer(s), such as a mainframe computer, a personal computer (desktop, laptop, tablet-type, or otherwise), a workstation, a minicomputer, a computer network, a "virtual network," a "internet cloud computing facility," a personal digital assistant, a smartphone, a tablet, or other handheld or mobile computing device.

According to embodiments, the electronic device 600 includes processing hardware 602 that includes a memory 604. As shown in FIG. 5, the computing device 600 also includes a processor 606 communicatively coupled to the memory 604, and an input and/or output (I/O) portion 608 communicatively coupled to the processor 606. The computing device 600 can further include an interactive hardware portion 610. The interactive hardware portion 610 is coupled to the I/O portion 608 such that a command or other input entered or provided by a user through the interactive hardware portion 610 will be forwarded to the I/O portion 608, to the processor portion 606, and then to the memory portion 604.

As shown in FIG. 6, the interactive hardware portion 610 can include one or more input devices 1612 (e.g., a keyboard, a mouse, a touch screen, a microphone, a stylus, a radio-frequency device reader, and the like) for receiving inputs from the user or other sources, a display device 614 for displaying content to the user on the computing device 600, and/or a data port 616 (e.g., USB, Fireware, Thunderbolt, etc.) for receiving or sending data via a data cable coupled to the data port 616. As shown the interactive hardware portion 610 can also include a communications module 618 (also referred to herein as a "wireless unit") comprising one or more transceivers and/or other devices for communicating with one or more networks (e.g., a wide area network (including the Internet), a local area network, a GPS network, a cellular network, a Bluetooth network, other personal area network, and the like). In the illustrated embodiment, the communications module 618 includes a data receiver 620 (e.g., similar to data receiver 20 shown in FIG. 1) for wirelessly receiving identification information from, for example, identification device 18 shown in FIG. 1 or access card 102 shown in FIG. 5, using a personal area network, such as, e.g., an RFID network.

The processor 606 can be a hardware device for executing software, particularly software stored in the memory 604, some of which may or may not be unique to the system 10 shown in FIG. 1. The processor 606 can be any custom-made or commercially available processor, a central processing unit (CPU), an auxiliary processor among several processors associated with the computing device 600, a semiconductor-based microprocessor (in the form of a microchip or chip set), another type of microprocessor, or generally any device for executing software instructions. The processor 606 may also represent a distributed processing architecture such as, but not limited to, SQL, Smalltalk, APL, KLisp, Snobol, Developer 200, MUMPS/Magic.

The memory 604 can include any one or a combination of volatile memory elements (e.g., random access memory (RAM, such as DRAM, SRAM, SDRAM, etc.)) and non-volatile memory elements (e.g., ROM, hard drive, tape, CDROM, etc.). Moreover, the memory 604 may incorporate electronic, magnetic, optical, and/or other types of storage media. The memory 604 can have a distributed architecture where various components are situated remote from one another, but are still accessed by the processor 606. The memory 604 may store software that includes one or more separate programs comprising ordered listings of executable instructions for implementing logical functions.

When the electronic device 600 is in operation, the CPU portion 606 can be configured to execute software stored within the memory 604, to communicate data to and from the memory 604, and to generally control operations of the electronic device 600 pursuant to the software. In some embodiments, the memory 604 includes a non-transitory computer readable medium for implementing all or a portion of method 700 shown in FIG. 7. The memory portion 604 may also be utilized to implement at least part of one or more databases utilized by the system 10, such as, for example, patient database 622 for storing patient information (e.g., patient history, pathology, and other private health information), medical information database 624 for storing medical information obtained using the medical device 10 or 100 (e.g., x-rays or other medical imaging data), and/or permissions database 626 for storing permissions information for each of a plurality of users authorized to use the medical device 10 or 100. In addition, the memory 604 can store one or more executable computer programs, such as, for example, an access control application 628, which may be executed by the computer processor 606 to carry out the principles disclosed herein (e.g., method 700). The executable programs can be implemented in software, firmware, hardware, or a combination thereof.

In one embodiment, the memory 604 stores both the permissions database 626 and the access control application 628. In another embodiment, the permissions database 626 and the access control application 628 are stored in different memories on different computers or servers. In some embodiments, all or portions of the permissions database 626, the patient database 622, and/or the medical information database 624 may be stored on a cloud server and may be accessible by the electronic device 600 to carry out the access control techniques disclosed herein. The memory 604 also includes an operating system 630 for controlling the execution of other computer programs, such as the access control application 628, and provides scheduling, input-output control, file and data management, memory management, and communication control and related services.

The access control application 628 may be a source program, executable program (object code), script, or any other entity comprising a set of instructions to be performed. When a "source" program, the program needs to be translated via a compiler, assembler, interpreter, or the like, which may or may not be included within the memory 604, so as to operate properly in connection with the operating system 630. Furthermore, the operating system 630 can be written as (a) an object oriented programming language, which has classes of data and methods, or (b) a procedural programming language, which has routines, subroutines, and/or functions, for example but not limited to, C, C++, Pascal, Basic, Fortran, Cobol, Perl, Java, .Net, HTML, and Ada.

If the electronic device 600 is a PC, workstation, PDA, or the like, the software in the memory 604 may further include a basic input output system (BIOS) (not shown in FIG. 6). The BIOS is a set of essential software routines that initialize and test hardware at startup, start the operating system 630, and support the transfer of data among the hardware devices. The BIOS is stored in ROM so that the BIOS can be executed when the electronic device 600 is activated.

Figure 7:
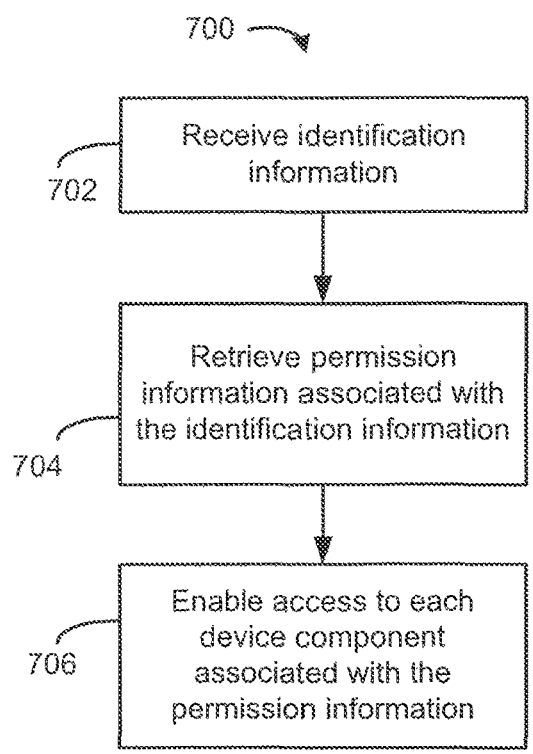
FIG. 7 is a flow diagram of an example method of controlling access to a medical device, in accordance with certain embodiments.

FIG. 7 illustrates an example method 700 of controlling access to a medical device, such as, for example, the medical device 12 shown in FIG. 1 or the portable x-ray machine 100 shown in FIGS. 2A-5, in accordance with embodiments. The method 700 can be carried out by a computing system included in the portable medical device, such as, for example, computing system 16 shown in FIG. 1 or electronic device 600 shown in FIG. 6. In one embodiment, the method 700 is implemented, at least in part, by data processor 606 executing software stored in memory 604, including access control application 628 shown in FIG. 6. In addition, to carry out the operations of the method 700, the computing system can interact with an identification device (e.g., identification device 18 shown in FIG. 1 or access card 102 shown in FIG. 5) via a data receiver (e.g., data receiver 20 shown in FIG. 1 or data receiver 620 shown in FIG. 6).

The method 700 can begin at step 702, where the data receiver wirelessly receives identification information for a user from an identification device associated with that user, via a wireless communication network, and provides the received information to the processor. As an example, in some embodiments, the data receiver may be an RFID reader configured to wirelessly communicate with an RFID device (e.g., tag) included in the identification device. In such cases, step 702 may include detecting an RFID device within a predetermined proximity of the RFID reader (e.g., using an interrogator signal) and obtaining the identification information from the detected RFID device.

At step 704, the processor retrieves permission information associated with the received identification information from the memory. The permission information identifies one or more components of the medical device as being permissible for access by a user associated with the identification device. At step 706, the processor enables access to each component identified by the permission information retrieved at step 704.

The one or more components of the medical device may be comprised of software, hardware, or a combination of both. As an example, the one or more components identified by the permission information may include a locking mechanism (such as, e.g., locking mechanism 106 shown in FIG. 2A) that is movable between a closed position preventing operation of the medical device (e.g., as shown in FIG. 2B) and an open position enabling operation of the medical device. In such cases, the processor may enable access to the locking mechanism by allowing movement of the locking mechanism to the open position. In some cases, the one or more components may further include a medical imaging device (such as, e.g., imaging head 108 shown in FIG. 2A) that is connected to the locking mechanism, and movement of the locking mechanism to the open position enables access to the medical imaging device. Also in some cases, the one or more components may include a user interface for controlling operation of the medical device (such as, e.g., user interface 110 shown in FIG. 3B), and movement of the locking mechanism to the open position enables access to the user interface.

In yet another example, the one or more components may include a transportation system (such as, e.g., transportation system 104 shown in FIG. 2A) having an unlocked mode for permitting transportation of the medical device and a locked mode for preventing transportation of the medical device. In such cases, enabling access to the transportation system includes placing the transportation system in the unlocked mode. The one or more components may also include a patient database comprising healthcare information for a plurality of patients (such as, e.g., patient database 622 shown in FIG. 6 and/or a data port for retrieving medical data from the medical device (such as, e.g., data port 616 shown in FIG. 6).

In certain embodiments, the process descriptions or blocks in the figures, such as FIG. 7, can represent modules, segments, or portions of code which include one or more executable instructions for implementing specific logical functions or steps in the process. Any alternate implementations are included within the scope of the embodiments described herein, in which functions may be executed out of order from that shown or discussed, including substantially concurrently or in reverse order, depending on the functionality involved, as would be understood by those having ordinary skill in the art.

It should be emphasized that the above-described embodiments, particularly, any "preferred" embodiments, are possible examples of implementations, merely set forth for a clear understanding of the principles of the invention. Many variations and modifications may be made to the above-described embodiment(s) without substantially departing from the spirit and principles of the techniques described herein. All such modifications are intended to be included herein within the scope of this disclosure and protected by the following claims.

The invention claimed is:

1. An x-ray device operable by a user, the x-ray device comprising:
   a plurality of device components, at least one of said components having at least one mode of operation available for selective enablement;
   a data receiver configured to wirelessly receive user identification information of a user;
   a memory module configured to store permission information associated with said user identification information, the permission information identifying permitted access of said mode of operation by the user; and
   a processor configured to receive the permission information from the memory module and based upon said permission information, enable access for said user to operate said mode of operation of said at least one of the components.

2. The x-ray device of claim 1, wherein the data receiver is configured to receive a radio frequency identification (RFID) associated with the user.

3. The x-ray device of claim 1, wherein said plurality of device components includes an x-ray imaging assembly component having a use mode and a calibration mode, wherein said processor is configured to selectively provide user access to operate either the calibration mode or the use mode of the x-ray imaging component based on the permission information.

4. The x-ray device of claim 1, wherein said at least one mode of operation includes access to a user interface configured to control functions of the x-ray device for generating an x-ray image.

5. The x-ray device of claim 1, wherein the one or more device components includes a medical imaging component and a locking mechanism, said locking mechanism having a first mode of operation configured to prevent operation of the medical imaging component and a second mode of operation for enabling operation of the medical imaging component.

6. The x-ray device of claim 5, wherein said processor is configured to enable access for a user to control a device component other than said medical imaging component.

7. The x-ray device of claim 6, wherein said at least one device component includes a drive mechanism having a wheel assembly for movement of the device, wherein said processor is configured to provide a user access to operate said drive mechanism while not a providing access to operate said medical imaging component.

8. An x-ray device, comprising:
   a plurality of device components operable by a user, each of said device components having one or more modes of operation available for selective enablement for use by the user;
   a data receiving module configured to receive user identification information of a user;
   a processor configured to:
      obtain permission information associated with the user identification information, the permission information identifying permitted access to at least one of said modes of operation, and
      use the permission information to provide the user access to operate one or more of said device components.

9. The x-ray device of claim 8, wherein the data receiver module is configured to receive a radio frequency identification (RFID) associated with the user.

10. The x-ray device of claim 8, wherein said plurality of device components includes an x-ray imaging component having a use mode and a calibration mode, wherein said processor is configured to selectively provide user access to operate either the calibration mode or the use mode of the x-ray imaging component.

11. The x-ray device of claim 8, wherein said processor enables access to a user interface configured to control multiple device components.

12. The x-ray device of claim 8, wherein the one or more device components includes a x-ray imaging component and a locking mechanism, said locking mechanism having a first mode of operation configured to prevent operation of the medical imaging component and a second mode of operation for enabling operation of the x-ray imaging component.

13. The x-ray device of claim 8, further comprising a memory configured to store the permission information in association with the user identification information, the processor retrieving the permission information from the memory upon receiving the user identification information.

14. An x-ray device, comprising:
   an x-ray imaging component;
   a data receiving module configured to receive user identification of a user; and
   a processor configured to retrieve permission information associated with the user identification, and to selectively enable a use mode of the x-ray imaging component based on the permission information.

15. The x-ray device of claim 14, wherein the use mode is one of a plurality of use modes, including an imaging mode for enabling use of the x-ray imaging component and a calibration mode for enabling servicing of the x-ray imaging component, wherein said processor is configured to selectively permit access to said imaging mode and prevent access to said calibration mode based on said permission information.

16. The x-ray device of claim 15, wherein the plurality of use modes further includes a patient information mode for enabling access to patient information, and wherein said processor is configured to selectively permit access to said imaging mode and said patient information mode, based on said permission information.

17. The x-ray device of claim 14, further comprising a transportation component and a transportation mode for permitting mobility of the x-ray device, wherein said processor is configured to selectively permit access to the transportation mode based on the permission information.

18. The x-ray device of claim 17, further comprising a locking mechanism configured to prevent operation of the x-ray imaging component when enabled and permit operation of the x-ray imaging component when disabled, said locking mechanism being enabled during said transportation mode.

19. The x-ray device of claim 14, further comprising a memory configured to store the permission information in association with the user identification, the processor retrieving the permission information from the memory upon receiving the user identification.

* * * * *